United States Patent [19]

Ji et al.

[11] Patent Number: 5,894,022

[45] Date of Patent: Apr. 13, 1999

[54] EMBOLIC MATERIAL FOR ENDOVASCULAR OCCLUSION OF ABNORMAL VASCULATURE AND METHOD OF USING THE SAME

[75] Inventors: Cheng Ji, Los Angeles; Guido Guglielmi, Santa Monica, both of Calif.

[73] Assignee: The Regents of the University of California, Oakland, Calif.

[21] Appl. No.: 08/946,608

[22] Filed: Oct. 7, 1997

Related U.S. Application Data

[63] Continuation-in-part of application No. 08/519,738, Aug. 28, 1995.

[51] Int. Cl.$^6$ .............................. A61F 13/00; A61K 9/14
[52] U.S. Cl. .............................................. 424/422; 424/484
[58] Field of Search ........................... 424/422, 484, 424/486, 499; 514/776, 938, 952, 937

[56] References Cited

PUBLICATIONS

Scheffel et al. "Albumin Microspheres for Study of the Reticuloendothelial System," J. of Nuclear Medicine, vol. 13, No. 7, pp. 498–503, Jul. 1972.

*Primary Examiner*—Thurman K. Page
*Assistant Examiner*—Sharon Howard
*Attorney, Agent, or Firm*—Daniel L. Dawes

[57] ABSTRACT

The present invention is an endovascular embolic composition. The embolic composition comprises a hydrophilic insoluble matrix having a microscopic mesh-like structure. The voids or intricacies of the matrix enclose droplets of aqueous solution as well as liquid oil. This structure is essentially equivalent to a "gel" structure with the insoluble matrix including both aqueous and oil droplets within its mesh. In creating the matrix a liquid oil base is mixed with an aqueous solution of a matrix base. The matrix base comprises an organic polymer such as a protein like albumin or its equivalent dissolved in an aqueous solution which may contain additional solutes. The matrix base solution is mixed and emulsified with the liquid oil base at a volume ratio ranging between about 1-to-1 and 1-to-5 respectively. To create the embolic composition the matrix base is then precipitated or cross-linked to form a gel with a mesh-like microscopic structure in which insoluble matrix surrounds and entraps both aqueous fluid and liquid oil. Preferably sclerifying agents are included within the composition so that scar tissue will develop to permanently occlude the embolized vasculature.

20 Claims, No Drawings

EMBOLIC MATERIAL FOR ENDOVASCULAR OCCLUSION OF ABNORMAL VASCULATURE AND METHOD OF USING THE SAME

This application is a continuation-in-part of application Ser. No. 08/519,738 filed on Aug. 28, 1995.

BACKGROUND OF THE INVENTION

1. Field of the Invention

The present invention relates to the field of endovascular embolic materials for embolization in abnormal microvascular beds or nidi, and in particular to a semisolid-semiliquid endovascular embolic multipurpose ointment and a corresponding soft particle form of embolic beads.

2. Description of Related Art

Endovascular embolic materials, which are currently used for embolization of abnormal microvascular beds or nidi, include injectable solid particles, sutures, fibers, tissue or sponge fragments, as well as liquid agents such as glues and emulsions. In the case of brain arteriovenous malformation embolization, almost all of the solid embolic materials are nonradio-opaque. Most of these materials are rapidly biodegradable; for example, Avitene fibers, sponge and dura fragments, protein microbeads and the like, which offer only temporary embolization. See Lon F. Alexander et al., "The History of Endovascular Therapy," Neurosurgery Clinics of North America, 5 (3) at 383–391 (1994). The nondegradable materials, such as polyvinyl alcohol (PVA) particles, silk sutures and the like, have a high rate of recanalization and collateralization that is, a tendency for blocked vessels to reopen and a tendency for parallel vessel paths to develop, respectively. This not withstanding that these materials may permanently remain at the embolized sites.

It is believed that the spontaneous thrombolysis (i.e., dissolving of the blockage) and angiogenesis (i.e., growth of new vessels) are the main contributing mechanisms to this recanalization and collateralization. Furthermore, these prior art types of solid materials usually tend to stay proximate to the injection site instead of moving into the nidus itself due to the lack of deformability of these materials. As a result, a considerable number of nidus vessels remain anatomically open even though the whole arteriovenous malformation nidus is angiographically occluded. These remaining portions, which lack embolic material, offer beds for recurrence. See for example Mazen H. Khayata et al., "Materials and Embolic Agents for Endovascular Treatment," Neurosurgery Clinics of North America, 5 (3) at 475–84 (1994).

Many liquid embolic materials have unfavorable properties. For example, while liquid glue, such as isobutyl-2-cyanoarylate (IBCA) has a good mobility rate inside the delivery microcatheter, it is unpredictable inside the nidus due to difficulties in controlling its polymerization rate. An optimal result may be achieved if a glue with suitable adjusted hardening time is delivered into the desired dominant portion of the arteriovenous malformation nidus. However, further treatment, such as surgical removal or radiation, is usually required in most cases using these liquid materials. See Fournier et al., "Endovascular Treatment of Intracerebral Arteriovenous Malformations: Experience in 49 Cases," Journal of Neurosurgery, 75 (2) at 228–33 (1991).

In the case of malignant tumor endovascular treatments, such as hepatocellular carcinoma embolizations, the liquid emulsions made of Lipiodol and aqueous anticarcinogenic solutions show much better effects than most solid drug carrier particles. This is because the liquid emulsions have better mobility and can embolize malignant microvascular beds more extensively than solid particles. In addition, the emulsion can carry more anticarcinogens into the tumor. See Ichida et al., "Therapeutic Effect of a CDDP-Epirubicin-Lipiodol Emulsion on Advanced Hepatocellular Carcinoma," Cancer Chemotherapy and Pharmacology, 33 suppl., S74–8 (1994).

However, nonsolidifiable liquid material, such as Lipiodol emulsion, cannot be applied in the treatment of arteriovenous malformation because the emulsion would be washed away within minutes. Liquid emulsions exhibit less friction in the embolized microvascular beds, so that in some high blood flow tumors, especially those with intratumoral microshuntings similar to the arteriovenous malformation nidi, the delivered embolic agent can be washed away within hours or days. See Kan et al., "Distribution and Effect of Iodized Poppyseed Oil in the Liver After Hepatic Artery Embolication: Experimental Study in Several Animal Species," Radiology, 186:861–6 (1993); and Luo et al., "Treatment of Hepatocellular Carcinoma by Transarterial Approach," Chung-Huai Hsueh Tsa Chih Chinese Medical Journal, 73:158–60 (1993).

What is needed is a more stable embolic carrier with a better relative friction and mobility to produce a longer lasting embolization for preventing or retarding thrombolysis or revascularization and for maintaining a higher drug concentration within the target tumors when used for drug delivery. Embolic agents that resulted in scar formation which blocks new vascular growth would be especially favored. Therefore in general what is needed is an improved therapeutic result in endovascular embolizations which is not subject to the disadvantages discussed above in connection with each of the prior art embolic materials.

BRIEF SUMMARY OF THE INVENTION

The present invention is an endovascular embolic composition. The embolic composition comprises a hydrophilic matrix having a solid microscopic frame-work or mesh that forms an essentially sponge-like structure having a semisolid/semi-liquid or spongy texture. The microscopic framework or intricacies of the matrix enclose aqueous solutions as well as liquid oil. This structure is essentially equivalent to a "gel" structure except that the insoluble matrix includes both aqueous and oil droplets within its mesh. In creating the matrix a liquid oil base is mixed with an aqueous solution of a matrix base. The matrix base comprises an organic polymer such as a protein like albumin or its equivalent dissolved in an aqueous solution which may contain additional solutes. The aqueous matrix base solution is mixed and emulsified with the liquid oil base at a volume ratio ranging between 1-to-1 to 1-to-5 aqueous to oil. To create the embolic composition the matrix base is then precipitated or cross-linked to form a gel, a material with a microscopic mesh in which the insoluble mesh surrounds and entraps both aqueous fluid and liquid oil.

For example, the emulsion can be heated in a water bath at a temperature of 50° C. to 100° C. to precipitate the matrix base as the sponge-like matrix mesh or frame-work. It will be apparent that the temperature and duration of heating will affect the final physical characteristics of the embolic composition so that compositions of almost any desired properties can be produced. When the matrix base (protein or other polymer) precipitates or coagulates, it captures and encloses aqueous solution as well as liquid oil base. These enclosed materials greatly influence the final physical properties with the liquid oil base reducing the frictional characteristics of the composition making it unusually slippery and greatly facilitating injection of the material through hollow needles, catheters and similar devices.

A great advantage of preparing the composition from an aqueous solution and a liquid oil is the ability to include medicaments that are either water soluble or liposoluble (oil soluble). Such as medicaments include hemostatics, positive electrical charge donators, sclerotic agents, anticarcinogens, radioactive agents and combinations of the same. Other embodiments of the embolic composition may further comprise liposoluble modifiers, such as phospholipids, water soluble modifiers such as polyethylene glycol, and stabilizing agents such as ascorbic acid (vitamin C) and tochopherol (vitamin E) to modify the physical properties of the composition and/or protect the added medicaments.

It will be appreciated that a major use for the present invention is the permanent occlusion of abnormal vasculature. Therefore, an important part of the invention is the inclusion of sclerotic agents such as tetracycline to permanently occlude the vasculature with scar tissue and hemostatic agents such as fibrinogen and thrombin to extend the composition produced blockade with a blood clot. The embolic composition may advantageously further comprise radio-opaque materials, such as metrizamide, tantalum, tungsten, other well-known radio-opaque agents and combinations of the same. These materials render the composition visible by x-rays so that physicians can readily monitor the administration of the composition. The radio-opaque agents can be dissolved in the aqueous solution of the matrix base or in the liquid oil base or may be insoluble materials merely suspended within the composition. For example, Ethiodol, a radio-opaque liquid oil, can comprise part or all of the liquid oil base.

In one embodiment of the embolic agent the aqueous solution of the matrix base and liquid oil base are emulsified and formed into particles of a predetermined size range. The particles then are suspended in a liquid medium. An alternative embodiment further comprises forming particles from the heated emulsion by quickly cooling the emulsion as it is expressed through a needle into a liquid, collecting the particles by filtration, and suspending the particles in a liquid medium such as normal saline. In another embodiment the invention comprises a homogeneous semiliquid-semisolid ointment.

The invention and its various embodiments may be better understood by now turning to the following detailed description.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved embolic composition for occluding abnormal vasculature.

The composition of the present invention is intended to provide a composition for use in a nonsurgical method of permanently embolizing abnormal vasculature, especially microvascular nidi. Abnormal vasculature must be repaired before a life threatening hemorrhage occurs. An equally important need for embolization is the blockage of vasculature feeding tumors. If the blood supply is cut off, growth of invasive tumors can be reduced or stopped. This is especially true if the embolizing agent delivers anti-cancer drugs at the same time that it blocks blood circulation.

Other nonsurgical embolizing agents suffer from being impermanent or, alternatively, from causing long term inflammation. If the agent consists of semisolid materials sufficiently liquid to ensure injection without requiring excessive pressure, the agent is likely to be rapidly broken up by blood flow and washed away. If the agent hardens (polymerizes) after injection, like cyanoacrylate glues, it is likely to result in tissue damage and long lasting inflammation. If the agent washes away or migrates, it can be very difficult to detect and monitor. The present invention largely obviates these problems by providing a unique matrix structure that resists break up and wash away. Oil included within the agent provides lubrication so that excess injection pressure can be avoided. The agent is readily rendered radio-opaque so that its administration and long term residence can be easily monitored. Addition of various active agents can ensure that the filled area is invaded and occluded by scar tissue. Other active agents ensure that clots develop around the injected composition to extend the occluded region. Further, the matrix can be prepared from nonantigenic materials so that long term inflammation is avoided.

The material of the present invention has certain compositional similarities to a topical ointment and, hence, may be colloquially referred to as an "ointment." Such reference should not be allowed to obscure the very real differences between the present invention and topical ointments both in composition and site and method of use. Most topical ointments or creams which are presently used contain, roughly, two major components, namely an aqueous part and an oil or hydrophobic part. Generally, an ointment or a cream represent an emulsion between these two components with ointments usually representing a water in oil emulsion and creams representing an oil in water emulsion. Either the aqueous and/or the hydrophobic component may contain any of a number of dissolved active ingredients and additives. In addition, matrix or filler materials soluble in neither of the two base materials may be dispersed in the final product. Generally, the matrix material contributes to the physical texture and related physical properties of the product.

The so-called ointment of the present invention is in a semisolid-semiliquid form. Like more typical ointments this composition is prepared from an aqueous portion and an oil or hydrophobic portion. In addition, an insoluble filler or matrix material such as clay is frequently added. However, unlike a typical ointment where the insoluble matrix material is merely dispersed within the emulsion, the matrix of the present invention forms an insoluble mesh or sponge-like structural frame-work which encloses droplets of both the aqueous and the oil base, more like a gel than a typical emulsion. This gel property gives the final composition two unique characteristics: (1) self-lubrication when disposed inside a delivery device such as a hollow needle or catheter; and (2) surface hydration when disposed inside blood vessels or other sites within the vascular system. Self-lubrication is provided by the liquid oil which oozes out of the mass and provides a slippery coating as well as reducing internal friction. Surface hydration is a property of the insoluble matrix mesh that is a result of the special characteristics of this material as elaborated below. In the present invention the precipitated matrix while at least partially insoluble is selected to be hydrophilic so that it becomes hydrated and may even swell to some degree. With these two unique characteristics, in addition to suitable mobility, viscosity, interfacial tension and friction, the composition of the present invention can readily pass through the smallest internal diameter needles and microcatheters with ease, and yet still offer maximum and stable embolization.

The gel-like enclosing properties of the matrix mesh allow any of a number of active ingredients or medicaments to be enclosed within the ointment of the present invention. Material can be dissolved in the aqueous component or in the oil or can be bound to the matrix mesh. Once a medication is so encapsulated, it is slowly released for a predetermined period of time, typically for several weeks from the injected emboli to cause local effects with minimal or no systemic side effects. The injected composition is eventually metabolized and/or infiltrated by cells and leaves an organized lesion. It will be apparent to one of ordinary skill in the art that a primary function of the injected composition is more than mere mechanical blockage; in fact, many of the prior art material discussed above provide only mechanical blockage. Equally important further functions of the invented composition, depends on the added medicaments. For example, an extremely effective composition can made by adding tetracycline, a common sclerotic agent to the general composition. The sclerotic agent causes organization of fibroblasts and related scar tissue into the treated nidus or vascular bed resulting in permanent occlusion of the injected structure.

Apart from the wide range of active additives, some of which will be addressed below, the compositions of the present invention can separated into two broad classes based on their overall physical properties: a multipurpose ointment (MPO) in a semisolid-semiliquid form and a multipurpose particle (MPP) in a soft solid particulate form. The compositions are prepared by combining or emulsifying an aqueous base containing a dissolved matrix base with a liquid oil base along with added modifiers and medicaments. The resulting emulsion is then treated to precipitate or coagulate a matrix mesh as a more or less insoluble material that encloses and entraps both the remaining aqueous base and the oil base in a gel-type structure. The degree to which the matrix is precipitated influences the final physical properties of the composition. The preferred matrix bases are soluble proteins such as human serum or chicken egg albumin. Many other soluble proteins are suitable as well as other organic polymers besides proteins and polymerizable monomers such as acrylamide. In a preferred composition the matrix is precipitated from the matrix base by heating to partially denature the protein. An alternate embodiment uses naturally precipitating proteins (e.g. enzymatic coagulation as in the formation of blood clots or the curdling of milk proteins). Obviously, other means of producing a gel-like structure with a microscopic matrix mesh from the matrix base are equally applicable to the present invention. For example, various chemical cross-linking agents could be added to form the matrix mesh from a matrix base of organic monomers. Other organic materials besides proteins (e.g. acrylamides) are especially susceptible to being polymerized to form a gel with a sponge-like insoluble or semi-soluble matrix mesh. In the MPO formulations the matrix gel is formed in bulk. The degree of cross-linking or denaturation serving to alter the viscosity of the final product. In the MPP formulations the matrix gel is formed in individual globules so that particles are formed having a more or less soft or spongy texture. These particles may be used directly (e.g. in an aqueous suspension) or they may be mixed into any of a number of emulsions or ointments including MPO compositions.

Both MPO and MPP forms of the present invention not only compactly fill most of a malformed arteriovenous nidus, but also inhibit angiogenesis and promote thrombogenesis as well as thrombus organization, thereby minimizing the anatomically empty portion of the treated vascular system. Therefore, a more complete and longer lasting embolization is produced, an embolization which is more likely to lead to a permanent cure for the arteriovenous malformation. In the case of high flow vascular tumor embolization, both forms offer a more complete and longer lasting chemoembolization than conventional embolic materials.

MPO represents a family of ointment-like, highly radio-opaque embolic materials. These embolic agents act like a multipurpose vehicle which can carry different medications and be delivered to target lesions through interventional devices, including but not limited to direct puncture needles, drainage tubes, endovascular catheters, and any type of delivery instrument now known or later devised. The MPO compositions can include a variety of sclerotic agents as well as other active medicaments. A particularly advantageous formulation contains ingredients intended to coagulate or clot blood proteins in close proximity with the composition, thereby extending the occluding effect beyond the physical boundaries of the material itself.

Various versions of MPO may contain different sclerosants, anticarcinogens, radioactive agents, antibiotics, electrical charges and biological agents of any kind now known or later discovered, including combinations of these agents. Therefore, MPO can be widely applied as embolic materials for tumors, arteriovenous malformations, varicose veins, cysts, bleeding vessels and any other endovascular disease or condition to which an embolism may be relevant. In addition to vascular applications, MPO can be advantageously used to occlude Fallopian tubes (i.e., used to effect female sterilization). To embolize arteriovenous fistula, or aneurysm, MPO may be applied in conjunction with other endovascular embolic materials, devices or methods, such as balloons and coils. The corresponding multipurpose particles, MPP, is useful for embolizing bleeding vessels, tumors, or arterio-veneous malformations.

The application of the multipurpose ointment, MPO, now having been described, its composition and manufacture will now be explored. The first of the two basic parts of the multipurpose ointment is the aqueous solution of the matrix base. The matrix base, may be comprised of, human serum albumin or chicken egg albumin or their equivalents. Acceptable albumins comprise nonantigenic, biodegradable and biocompatible materials, which are already widely used and available clinically as microspheres and microcapsules. Some of these microspheres, in fact, were originally designed for use in endovascular chemoembolizations.

Equivalent materials which could replace or mix with the albumin to form the matrix base have the following two properties as of albumin: (1) solubility in aqueous solutions; and (2) the ability to coagulate or solidify encapsulating the aqueous solution to form an insoluble, microscopic matrix mesh after adequate heating or certain other physical or chemical treatments. Such materials include other globular proteins, collagen, fibronectin, laminin and similar proteins or other monomers or polymers now known or later discovered.

The aqueous solution of MPO functions as a solvent for the matrix base (e.g. albumin and the like). This aqueous solution typically is, but is not limited to, contrast-medium solutions, such as Omnipaque manufactured by Sterling Pharmaceuticals, Inc. Sterile water, normal saline, buffer solutions and all similar solutions now known or later discovered can also function as the solvent of the matrix base.

The second basic part of MPO, the liquid oil base, is comprised of an iodized oil, such as Ethiodol as manufactured by Savage Laboratories, a division of Altana Inc. of Melville, N.Y. Omnipaque and Ethiodol are two kinds of contrast agents widely used clinically for angiography and lymphography, respectively.

In addition to these two basic parts, MPO may include optional agents to modify mobility, viscosity, deformability, elasticity, surface tension and frictional properties. For example, the following optional materials may be added, all of which are nontoxic, nonantigenic and biocompatible:

a). lipid soluble modifiers, such as cholesterol, bone wax, phospholipids, mixed with Ethiodol;

b). water-soluble modifiers, such as polyethylene glycol, povidone (polyvinylpyrollidone), dextran, starch, chitin, chitosan, gelatin, alginate, DNA and the like, can be dissolved in aqueous protein solutions;

c). surfactants, emulsifiers, cross-linking agents and stabilizing agents such as polysorbate and vitamin C can also be added to provide a stable mixture; and d). radio-opaque materials, such as powders of metrizamide, tantalum or tungsten to enhance fluoroscopic visibility.

This listing is illustrative only and is not intended to limit the scope of the present invention which includes all modifiers now known or later devised.

Examples of the medication which may be added as optional materials include, but are not limited to:

a). hemostatics, such as thrombin and the like (but note that, as explained below, some hemostatic agents may be used as the major component of the matrix base solution);

b). positive electrical charge donators, such as stearylamine and the like, used for promoting thrombogenesis;

c). sclerosants, such as tetracycline, deoxycycline and the like, for sclerosing the embolized vessels;

d). radioactive materials, such as $^{131}$ iodine labeled Lipiodol, $^{32}$P colloid, $^{90}$Y powders and the like, used for internal radiation therapy to control both angiogenesis and proliferation of malignant cells.

e). antineoplastic agents, such as cis-platinum, adriamycin and the like for killing malignant cells.

Again, this list is illustrative only and is not intended to limit the scope of the present invention which includes all medications now known or later devised. Medications delivered with MPO are intended for their own original or unique purposes apart from embolization. The local effects of these agents is increased at the delivery site by their proximity, while their toxicity to the overall system is decreased.

The application and the composition of the multipurpose ointment now having been described, consider methods by which the ointment may be prepared. In the simplest case the matrix microscopic mesh is precipitated from the aqueous matrix base by heat which partially denatures the soluble matrix material. Albumin or its equivalent is dissolved into an aqueous contrast-medium solution. For example, 50 to 400 milligrams of the albumin can be dissolved per cubic centimeter of the contrast-medium solution. Water soluble medications and modifiers can then be added after the albumin is in solution, and/or lipid soluble medications and modifiers can be added to the oil base. The aqueous solution is then mixed with Lipiodol at the rate of 1-to-1 to 1-to-5 in volume ratios respectively. This mixture is then completely. The emulsion is heated in a water bath to a temperature approximately in the range of 50° C.–100° C. to denature the albumin and precipitate it as a matrix mesh which encapsulates both the liquids.

The final product is comprised of MPO with the precise preparation parameters being chosen in order to obtain the desired deformability, elasticity, viscosity, as well as self-lubrication and surface hydration. The concentration of albumin, the degree of emulsification, and the degree and duration of heating significantly modify the physical characteristics of the MPO and, therefore, are manipulated according to the end characteristics desired in any given application. That is, increased concentrations of the matrix base and longer heating at higher temperature will result in a material with a harder or more resilient texture.

MPO1 Example

Preparation of MPO1, is an embolizing agent for arteriovenous malformation in the brain, contains the basic MPO composition with functional medications, such as sclerosing agents tetracycline and its analog deoxycycline. MPO1 is improved over conventional embolic materials in that it is: (1) highly radio-opaque and clearly visible with X-ray fluoroscopy; (2) very controllable when delivered through a microcatheter; (3) effective for permanent occlusion or sclerosing of the vessel lumens by means of fibroblasts; and (4) safe, since the chemically induced inflammatory reaction is limited to vessel lumens and then only for a very short period of time.

In this example, 150 milligrams of albumin from chicken egg, grade V, Sigma Chemical Company of St. Louis, Mo., and 250 milligrams of tetracycline hydrochloride are first dissolved in 1 mL of Omnipaque aqueous contrast-medium to constitute the aqueous matrix base. The solution is blended and emulsified with Ethiodol (the oil-base) until the total volume reaches 5 milliliters. The final mixture is then heated at approximately 58° C. in a water bath for 10 minutes. The MPO1 is prepared under aseptic conditions and then stored at 4° C.

Each milliliter of MPO1, thus contains 30 milligrams of albumin, 50 milligrams of tetracycline, 0.2 milliliters of Omnipaque and 0.8 millimeters of Ethiodol. The MPO1 was injected through a number 25 needle into a small cup with normal saline for evaluating its solubility in water. To test the friction between MPO 1 and the microcatheters, 0.2 milliliters of MPO1 was injected into a Tracker 18 catheter (Target Therapeutics Inc. San Jose, Calif.) using normal saline or 20 percent fat emulsion to push the MPO1 through the catheter. The pressure required to push the MPO1 out of the catheter was recorded. The same test was repeated with a Tracker 10 catheter, and Magic 1.8 and Magic 1.5 catheters (Balt, Montmorency, France). The test was also repeated after MPO1 had been stored at 4° C. for 1, 2, 3 or 4 months.

The friction tests show that the pressure required for pushing 0.2 milliliters of MPO 1 with normal saline through a Tracker 18 microcatheter is always below 70 psi and less than 100 psi for a Tracker 10, 120 psi for a Magic 1.8, and 150 psi for a Magic 1.5. When the test is repeated with 0.1 milliliters of MPO1 in a Magic 1.8, the pressure is less than 80 psi, and less than 110 psi for a Magic 1.5. When a 20 percent fat emulsion instead of saline is used to push the ointment through the catheter, the pressure is reduced about 20%, for example, 65 psi for a Magic 1.8 and 90 psi for a Magic 1.5. The test repeated with MPO1 stored for up to four months gave the same results.

The in vitro evaluation disclosed that MPO1 is insoluble in normal saline. Shortly after it is injected into the saline, the surface of the MPO becomes white and swollen due to hydration. After three months of storage, however, the color begins to change from bright yellow to brown which change is believed to be due to decomposition of the tetracycline. No other changes were found in MPO.

MPO1 has the characteristics of both solid and liquid materials. The its apparent solidity allows MPO1 to occlude small vessels. Furthermore, the surface hydration increases the friction between the vessel intima and MPO1, which helps to block the vessels. Liquidity as well as its self-lubrication makes MPO1 easier to inject through microcatheters. It is know that hand injection with a one cc syringe can easily produce pressures of 400 psi. The rupture pressure for Tracker catheters is designed at about 500 psi. However, the rupture pressure for the Magic system or flow-direct microcatheters is about 200 psi, and the recommended injection pressure should not exceed 100 psi. Given these restrictions and the results of the friction test, the use of higher pressure catheters is recommended in connection with MPO1 and special attention should be paid to reduction of the pushing pressure, such as by inclusion of a 20 percent fat emulsion.

Consider now an in vivo test of MPO1 prepared as described in the example above. Ten swine of mixed sexes, weighing 50 to 60 pounds each, were used for the in vivo study. Animals 1–6 underwent embolization of rete and the ascending cervical artery using MPO1. Animals 7 and 8 underwent embolization of lung and rete with MPO1, and the ascending cervical artery with the generic MPO. Animals 9 and 10 underwent bilateral rete embolization with conventional PVA particles as a control. Angiography was performed just before and immediately after the embolizations and followed up at one and two week, and at one, two, three and six-month intervals thereafter. Animal 1 was sacrificed on the first day, animal 2 at two weeks following embolization, animals 3, 4 and 7 at two months, animal 8 at three months, and animals 5, 6, 9 and 10 at six months. All vessels and lungs which were embolized were harvested for pathological study. Samples of spleen and lymph nodes were collected for histological study and all other organs were subjected to gross examination.

In the swine, no recanalization, that is reopening of the feeding arteries, was found angiographically for up to six months in the MPO1 group. However, recanalization occurred in all the conventional PVA embolized retes. The degree of feeding artery reopening is between 20 and 80% and tends to increase with time. A normal rete is fed mainly by the ascending pharyngeal artery and also is partially supplied by a small branch from the middle meningeal artery. This small feeder acts like a collateral artery. After the main feeder pharyngeal artery and the rete is embolized with conventional PVA particles, the immediate post embolization angiographies show that 20 to 35% of the rete microvasculatures, which obtain blood supply from the collateral branch, remain patent or unembolized. However, in the group of animals treated with MPO1, only 0–10% of the rete remain open. Follow-up angiographies of the conventional PVA group show the middle meningeal branch enlarges with time and its feeding portion of the rete extends into the previously embolized portion. The percentage of the patent vessels in the rete increases up to 50–70%. However, in the MPO1 group, follow-up angiographies show no change or very small changes in size of the collateral branch and its domain.

No recanalization is found in ascending cervical arteries embolized with MPO 1, but the arteries embolized with MPO all reopen completely within two weeks. All swine included in the study were healthy until sacrificed and no abnormal behaviors were found. Two of the animals underwent pulmonary artery embolization with MPO1. One was embolized into a surgically constructed arteriovenous fistula. The other was embolized directed into pulmonary arteries via venous approach. The total amount of MPO1 for each animal was 1.0 milliliters with follow-up chest radiographs showing normal findings. After sacrifice, the brain, liver, spleen and kidney were grossly examined. No infarctions or inflammations were found.

No significant infarctions of approximately were found in the lungs following pulmonary artery embolization. Embolized retes and ascending cervical arteries appeared harder than unembolized vessels. The adventitia appeared normal and no adhesion or edema were found in surrounding tissues. Histopathological studies indicated that the vascular lumps from the size of 50 µm to 2.0 mm were filled homogeneously with MPO1. On the same day as embolization, no signs of inflammatory reaction were found. Two weeks after embolization, chronic inflammatory response was seen inside the vessel lumens. Macrophages and lymphocytes infiltrated into the MPO1. Granulation tissue instead of MPO1 filled the entire lumens of microvessels which were less than 300 µm in diameter. In small (300 µm to 1.0 mm) and in middle sized (1.0 to 2.0 mm) vessels, MPO1 remained in the center of the lumens and the granulation tissue extended from the vessel wall into the MPO1.

Two months after embolization, fibroblasts and collagen fibers instead of macrophages became the dominant elements filling the vessel lumens. In microvessel lumens, mature scar tissue formed. However, granulation tissue could still be seen in small vessels and some chronic inflammatory cells remained in the lumen centers. Some MPO1 still remained in the center of some of the larger vessels.

At six months after embolization, also most all vessel lumens were filled with scar tissue. MPO 1 could only be detected in one or very large vessels.

Fluorescent microscopy confirmed that the vessel walls were intact. The internal elastic laminas were preserved. At two weeks after embolization, minimal amounts of chronic inflammatory cells were found infiltrating the vessel walls including the adventitias. However, this phenomenon disappeared at two months and there was no necrosis or other damage.

MPO1 may be sterilized by any means now known or later devised with electron beam radiation or gamma-ray radiation being presently preferred. Sealing the material in a package filled with nitrogen instead of air can avoid tetracycline oxidation. Avoidance of light exposure and the addition of certain reductive agents, such as Vitamin C, may further protect MPO1 from decomposition.

Most of the components of MPO1 are FDA approved safe agents, including tetracycline, Ethiodol and Omnipaque. Chicken egg albumin has been investigated as a drug-carrying material for oral and parental applications in several pharmacological labs. Either human or egg albumin may be used and is believed to be a safe material. No allergic reaction has been observed. However, some individuals may be allergic to the egg albumin, especially given a history of food allergy to egg products. Most of these patients have only a temporary skin reaction, and very rarely experience asthma or serum sickness. The use of human serum albumin is believed to be a safer material and is preferred over egg albumin making the MPO. There can be some danger of contamination of serum albumin with pathogenic viruses; however, the heat treatment used to precipitate the albumin is believed to limit this danger.

The use of tetracycline as a sclerosing agent has long been established and has been reconfirmed by the study discussed above. Without the tetracycline, MPO has been observed to offer only a temporary embolization. This kind of temporary effect is often seen with biodegradable materials, such as Avitene which is a bovine collagen fiber. The zero recanalization rate as well as the ability to inhibit collateralization, are advantageous features of MPO1.

The process of MPO1 metabolization and organization is observed to be similar to the natural consequences of thrombosis. This makes MPO1 superior to the nondegradable materials used in the prior art with which chronic stimulation and inflammation may persist for years following use.

The dosage of MPO1 applied for clinical procedure can be less than 5 milliliters which would contain 250 milligrams of tetracycline. This amounts to only 25 percent of a one day dosage for antibacterial therapy, and at this low level, systemic side effects of tetracycline are minimal.

The leakage of MPO1 from an arteriovenous malformation to the lungs may occur clinically, although the animal study above did not show any significant leakage from the retes to the brain. However, MPO1 is clearly visible with X-ray and small amounts of leakage down to 0.02 milliliters can be easily detected during the embolization procedure. Once an unacceptable leakage, for example on the order of 0.4 milliliters occurs, the physician can stop the delivery of MPO1, embolize the large shunting fistula within the arteriovenous malformation with other devices, such as coils, and avoid further leakage from any further MPO1 embolization. Furthermore, the above study shows that up to 1.0 mm of MPO1 embolized to the lungs causes no significant lung infarction. This is because lung tissue usually obtains its blood supply from two different vascular systems: the pulmonary artery, and the branchial artery system. If small amounts of MPO1 occlude some small branches of the pulmonary system, the blood supply from the branchial system is not affected. Therefore, there is no tissue death and there is unlikely to be any clinical consequences.

A different variety of MPO, named MPO02, can be formulated to take advantage of hemostatic agents to help extend the clot formed around the MPO. A number of natural clotting factors are usable in the present invention, but fibrinogen is particularly favored. This water soluble protein is present in large amounts in blood plasma and is readily available as a byproduct from plasma fractionation. Fibrinogen is readily cleaved to form a water insoluble protein known as fibrin which acts as a monomer and can be readily cross-linked to form the body of a blood clot (blood cells and other material are entrapped, thereby contributing to the total clot). An important advantage of formulations containing natural clotting agents is that the embolized area may well extend beyond the actual boundaries of the injected material as clotting materials are recruited and the resulting blood clot expands. This may result in embolizing a multifeeder arteriovenous malformation through injection of the main feeder only. Both the cleavage of fibrinogen and the polymerization of fibrin are catalyzed by the enzyme thrombin during the natural process of thrombogenesis at body temperature. However, thrombin, like many other enzymatic proteins, is quite heat labile. Therefore, one must avoid excessive heating during the preparation of fibrinogen/thrombin based MPO2.

The procedure for producing MPO2 is similar to that for MPO1 except that the matrix is formed by cross-linking fibrin rather than by heat precipitation of albumin. The matrix base comprises 50 mg of fibrinogen (Fraction I, ICN Pharmaceuticals, Costa Mesa, Calif.) and 100 mg of human serum albumin (Sigma Chemical Co., St. Louis, Mo.) are dissolved in 1 mL of normal saline (0.9% NaCl) or in 2 mL fresh human plasma to form the aqueous base. Ten to 50 mg of deoxycycline as a sclerosing agent are added. The final aqueous base solution is emulsified with Ethiodol at a ratio of between 1:1 and 1:4. Immediately prior to the emulsification process the aqueous base is "activated" by the addition of 0.2 mL of reaction agent. The reaction agent is an aqueous solution of calcium chloride (30 mmol/L) to which has been added 5 μg of thrombin (Parke Davis, Morristown, N.J.). Optionally, Factor XIII and other chemicals or clotting agents can be added to stabilize the fibrin cross-linking. The cross-linking reaction is complete within 5–20 min at room temperature.

It will be appreciated that "cold" polymerization is necessary to allow natural fibrin clot formation. When this material is used, active thrombin will recruit clotting proteins surrounding the site of embolization to further stabilize the injected embolic material. Similar "cold" or room temperature polymerization is required with any of a number of enzyme containing or enzyme precipitated mixtures such as the precipitation of milk proteins (lactoglobulins) with rennin or the polymerization of actin or actin and myosin under the influence of elevated calcium levels. It will be understood that a large number of cytoskeletal or cellular adhesion proteins are useful in the present invention. In addition, "cold" polymerization can be used with any of a number of organic molecules. Water soluble cross-linking agents such as water soluble carbodiimides can be used to cross-link soluble proteins such as albumin to produce a gel-like matrix at room temperature. In addition, water soluble monomers such as acrylamide can be polymerized into a gel either by addition of a catalyst such as ammonium persulfate or by photopolymerization using a mediator such as riboflavin.

An additional application of MPO is in female sterilization by occluding the Fallopian tube. Traditionally such sterilizations are carried out by ligation of the tubes. However, this procedure is somewhat invasive and is very difficult to reverse due to damage to a large portion of the Fallopian tube. The present inventors have discovered that the tubes can be permanently blocked by injecting approximately 0.01 ml of MPO1 into the Fallopian tube approximately 1 cm above the tube's junction with the uterus. This can be readily carried out with, for example, a Track-18 microcatheter. Since the Fallopian tubes are notoriously effective at expelling foreign material, the injected MPO1 is advantageously held in position by insertion of a small platinum wire coil on the uterus-side of the obstruction. Within two weeks scar tissue has formed which permanently closes the tube. Because only a small and discrete portion of the tube is blocked, the procedure can be reversed by cutting out the blocked region and reanastomosing the tube ends.

A second embodiment of the invention involves the use of soft solid particles or multipurpose particles (MPP). All types of ointment discussed above can have a sister or corresponding particle-form product derived from a modification in the preparation technique. Like the multipurpose ointment, these flexible particles are soft and have excellent deformability, which allows easy access into the embolizing vascular beds or nidi, and which leads to a more complete embolization than using conventional particles. In addition, the MPP particles are radio-opaque and, hence, easily visible under fluoroscopic monitoring. This opacity helps avoid pulmonary embolization and infarction, an iatrogenic or physician-induced complication of transcatheter embolization which may occur with radio-invisible material, such as polyvinyl alcohol particles. As in the case with other drug-carrier particles, MPP slowly releases included medication at the site of embolization to reach the highest local effects without significant systemic disturbance.

The preparation of MPP entails the same materials as the corresponding MPO materials with the exception of changes in the mixing rates and modifiers. Again, an emulsion is made between the matrix base, an aqueous albumin (or other protein or coagulatable material) solution with medications as may be needed, and the oil base, preferably an iodized oil such as Ethiodol. However, in the case of MPP the matrix is created in a particulate for by injecting the emulsion into a hot Ethiodol solution at about 100° C. through a fine needle. The inner diameter of the needle acts as a maximum particle-size grader. Liposoluble modifiers may be added to modify the particle surface. After a quick cooling, 1 to 5 times of the volume of ethanol is mixed into the Ethiodol solution to dilute it. The particles can then be separated by filtration and suspended in liquid medium such as contrast medium solutions. The heating temperature, cooling speed and surface modifications all alter the final deformability of these particles. The deformability of particles as well as their radio-opaque visibility distinguishes MPP from other currently available embolic particles. Of course, in the case of alternative coagulation methods such as enzymatic or chemical reactions the particles can be formed by injecting the emulsion into a reaction solution containing the enzyme or chemical catalyst that induces coagulation. An additional variation is available by mixing the particles into MPO. In this case the matrix is available both in the form or particles and as the amorphous ointment.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In addition to the equivalents of the claimed elements, obvious substitutions now or later known to one with ordinary skill in the art are defined to be within the scope of the defined elements.

We claim:

1. An injectable embolic material for occlusion of vascular elements and fallopian tubes produced by the process comprising the steps of:

preparing an aqueous matrix base comprising an aqueous solution of a matrix material capable of forming an insoluble matrix mesh;

making an emulsion of the matrix base and a liquid oil base; and treating the emulsion to form an insoluble matrix mesh from the soluble matrix base, the insoluble matrix mesh forming a microscopic porous structure with the liquid oil base and the aqueous solution enclosed in intricacies thereof.

2. The embolic material of claim 1, wherein the emulsion is formed into particles prior to formation of the insoluble matrix.

3. The embolic material of claim 1, wherein the matrix material is selected from the group consisting of albumin, gelatin, fibrinogen, lactoglobulin, immunoglobulin, actin, and acrylamide.

4. The embolic material of claim 1, wherein the aqueous matrix base further includes a medicament.

5. The embolic material of claim 4, wherein the medicament is a sclerosant.

6. The embolic material of claim 1, wherein the aqueous matrix base further includes a water soluble radio-opaque material.

7. The embolic material of claim 1, wherein the liquid oil base comprises a radio-opaque oil.

8. The embolic material of claim 1, wherein the insoluble matrix is formed by heating the emulsion to precipitate the matrix material.

9. The embolic material of claim 1, wherein the insoluble matrix is formed by an enzymatic reaction involving the matrix material.

10. The embolic material of claim 1, wherein the insoluble matrix is formed by a chemical polymerization reaction involving the matrix material.

11. The embolic material of claim 1 further comprising an insoluble radio-opaque material.

12. An improved embolic material of the type used to occlude vascular elements and fallopian tubes by injection therein, wherein the improvement comprises employing a semi-solid/semi-liquid material in which a matrix base is insolubilized to entrap an aqueous solution and a liquid oil base.

13. The improved embolic material of claim 12, wherein the liquid oil base is radio-opaque.

14. The improved embolic material of claim 12, further comprising a sclerosant for encouraging formation of scar tissue in the occluded lumens.

15. An injectable embolic material for occlusion of vascular elements and fallopian tubes produced by a process comprising the steps of:

preparing an aqueous matrix base comprising an aqueous solution containing fibrinogen; adding a sufficient concentration of calcium and thrombin to ensure enzymatic conversion of the fibrinogen to the aqueous matrix base;

making an emulsion of the matrix base and a liquid oil base; and allowing the emulsion to react enzymatically so that an insoluble microscopic fibrin mesh is created, the insoluble fibrin mesh forming a semi-liquid/semi-solid material with the aqueous solution and the liquid oil base enclosed in intricacies of the fibrin mesh.

16. An embolic material used to occlude vascular elements and fallopian tubes, comprising a semi-liquid/semisolid material wherein a water insoluble microscopic mesh of fibrin entraps an aqueous solution and a liquid oil.

17. The embolic material of claim 16, wherein the aqueous solution further includes a medicament.

18. The embolic material of claim 17, wherein the medicament is a sclerosant.

19. The embolic material of claim 16, wherein the aqueous matrix base further includes a water soluble radio-opaque material.

20. The embolic material of claim 17, wherein the liquid oil base comprises a radio-opaque oil.

* * * * *